United States Patent [19]

Nickerson, Jr. et al.

[11] Patent Number: 5,691,482

[45] Date of Patent: Nov. 25, 1997

[54] ADHESIVE SHEAR STRENGTH TEST APPARATUS

[75] Inventors: Earl S. Nickerson, Jr., Little Compton; Wayne C. Tucker, Exeter, both of R.I.

[73] Assignee: The United States of America as represented by the Secretary of the Navy, Washington, D.C.

[21] Appl. No.: 682,898

[22] Filed: Jul. 11, 1996

[51] Int. Cl.⁶ ............................................. G01N 3/08
[52] U.S. Cl. ........................................ 73/842; 73/827
[58] Field of Search ........................ 73/841, 842, 845, 73/847, 826, 827

[56] References Cited

U.S. PATENT DOCUMENTS

| | | | |
|---|---|---|---|
| 2,720,106 | 10/1955 | Lippman | 73/842 |
| 3,577,775 | 5/1971 | Henderson | 73/827 |
| 4,993,268 | 2/1991 | Thompson | 73/842 |

FOREIGN PATENT DOCUMENTS

| | | | |
|---|---|---|---|
| 0191847 | 8/1991 | Japan | 73/842 |
| 1280490 | 12/1986 | U.S.S.R. | 73/842 |

*Primary Examiner*—Elizabeth L. Dougherty
*Assistant Examiner*—Max H. Noori
*Attorney, Agent, or Firm*—Michael J. McGowan; Robert W. Gauthier; Prithvi C. Lall

[57] ABSTRACT

An apparatus for testing adhesive shear strength having a cylindrical adhesive bond between test specimens which is subjected to pure shear. The test specimens are two cylindrical rods. One rod has a bore and counterbore reamed into one end along its longitudinal axis. The other rod has a diameter essentially equal to the diameter of the bore. The adhesive to be tested is placed within the bore and counterbore and the smaller diameter rod is inserted into and seated at the base of the bore. The adhesive fills the space between the smaller rod and the counterbore, creating a uniform, cylindrical layer of adhesive between the exterior surface of the smaller rod and the inner surface of the counterbore. When the adhesive cures, the assembly is subjected to a tensile load along its longitudinal axis, tending to pull the inserted rod from the bore and subjecting the cylindrical adhesive bond to a pure shear load.

11 Claims, 2 Drawing Sheets

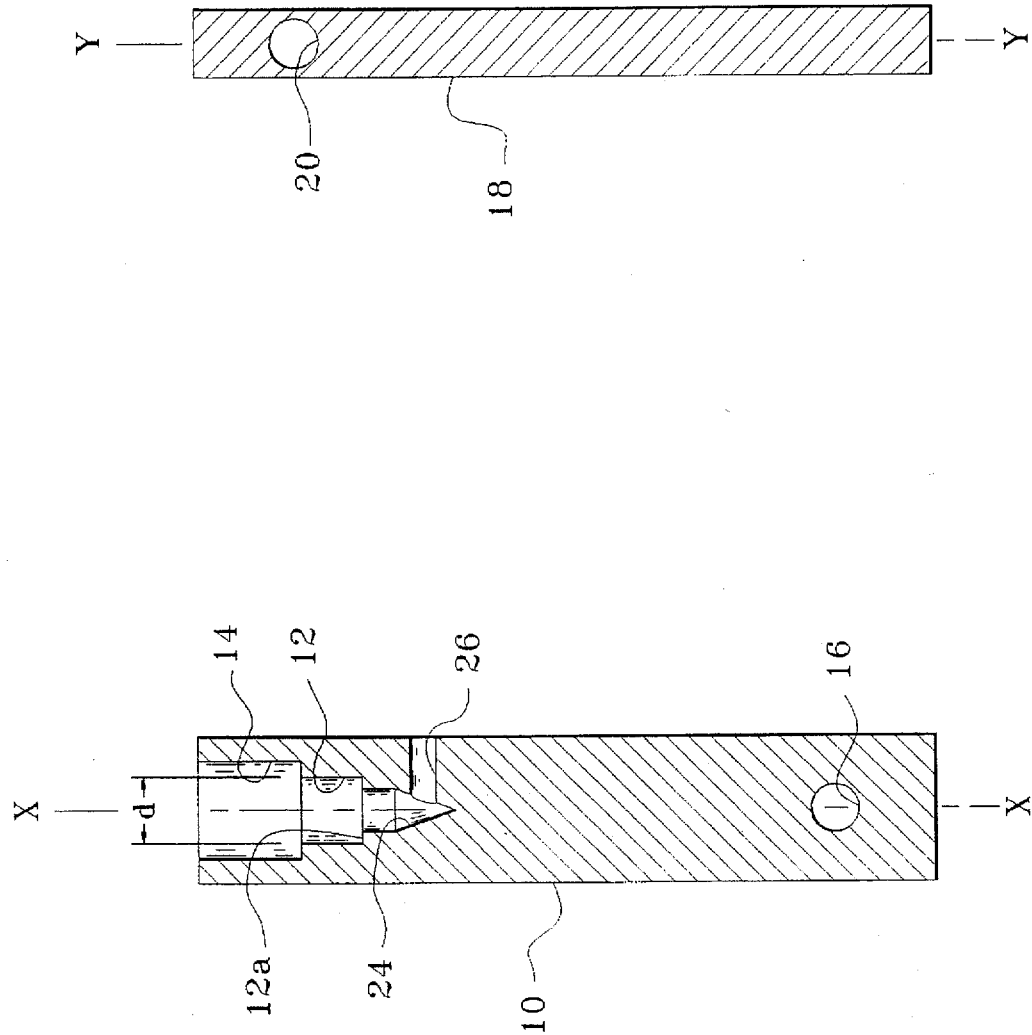

ADHESIVE SHEAR STRENGTH TEST APPARATUS

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates to testing adhesives and more particularly to testing adhesive strength in pure shear.

(2) Description of the Prior Art

In designing an adhesively bonded joint, it is necessary to determine the bonding strength of the proposed adhesive. Standardized test methods have been developed for testing the shear strength of adhesives, such as American Society for Testing and Materials tests, D3164-92a, "Strength Properties of Adhesively Bonded Plastic Lap-Shear Sandwich Joints in Shear by Tension Loading" and D3165-95, "Strength Properties of Adhesives in Shear by Tension Loading of Single-Lap-Joint Laminated Assemblies". Though these test methods are useful in determining comparative shear strength data, both tests utilize lap joints. In these tests, adhesive is placed between two overlapping plates and tension is applied to the ends of the plates furthest from the joint such that a shearing force is applied to the adhesive. However, bending forces are also introduced into the adhesive joint due to the lapped arrangement of the joint and the resulting offset in the tensile loading. The use of doublers, or offset plates, may be required to prevent bending failure of the adhesive joint. Further, the thickness of the lap-joint is difficult to control in that higher viscosity adhesives would typically result in a thicker joint. The lack of control leads to variability in test results from one specimen to the next.

SUMMARY OF THE INVENTION

Accordingly, it is a general purpose and object of the present invention to provide an apparatus for testing adhesive shear strength which subjects the adhesive bond to pure shear.

Another object is to provide an adhesive shear strength test providing greater control of bond, or adhesive thickness. A further object is to provide an adhesive shear strength test having less statistical variation between similar specimens.

These objects are accomplished with the present invention by providing new rod-shaped test samples to replace the lapped plates of previous test methods. A bore and a counterbore of slightly larger diameter are drilled into the end of the first rod. The second rod has a diameter essentially equal to the diameter of the bore. Adhesive is placed in the bore and counterbore of the first rod and the second rod is then placed into the bore, extending out of the counterbore, thus forming a cylindrical adhesive joint between the rods at the counterbore. The difference in diameter between the bore and the counterbore determines the thickness of the adhesive bonding the two rods. An axial tensile force is applied at the ends of the rods furthest from the joint, putting the joint into shear. Since the tension is axial, no bending is induced in the adhesive joint. The rods can be fabricated of metal such that they can be reused by burning off old adhesive in a furnace. Further, the rods and the drilled bore and counterbore can be accurately machined such that bond thickness does not vary between tests of different adhesives. Additionally, a number of rods can be fabricated with differing counterbore diameters which provide test data for a range of adhesive thicknesses resulting in a strength to thickness curve for the adhesive tested.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein:

FIG. 1 shows a cross section of a first rod used in forming the test sample for the adhesive shear strength test of the present invention;

FIG. 2 shows a cross section of a second rod used in forming the test sample.

DESCRIPTION OF THE PREFERRED EMBODIMENT

Figure 3:
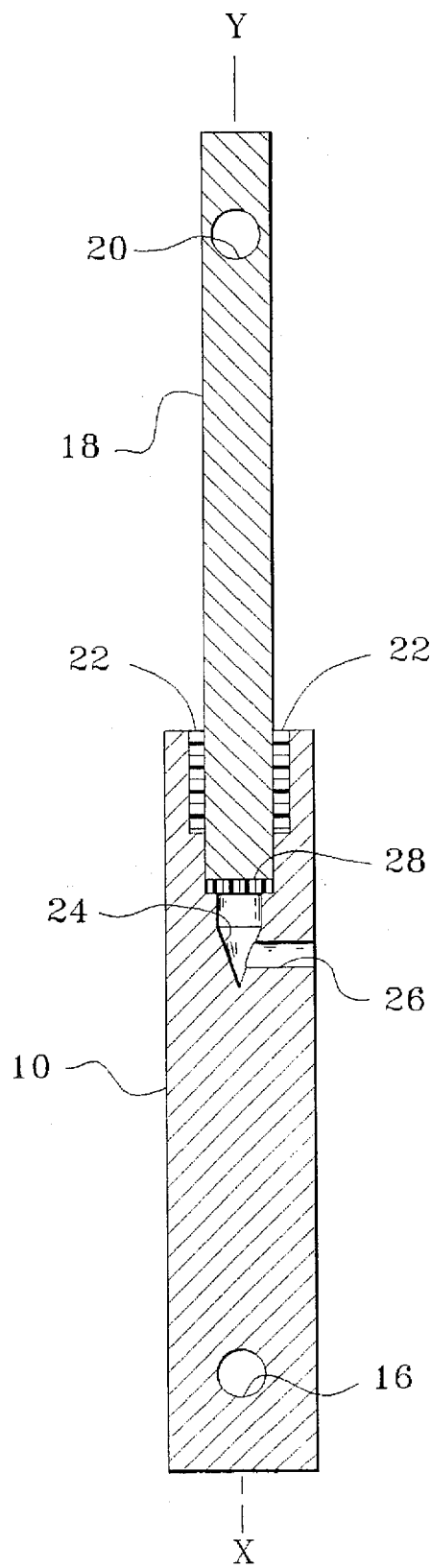
FIG. 3 shows a cross section of the rods in an assembled position for the adhesive shear strength test of the present invention.

Referring now to FIG. 1, holder rod 10 is shown in cross section. Holder rod 10 is cylindrical in shape having a bore 12 reamed along the longitudinal axis X—X at end 10a of holder rod 10. Bore 12 has a diameter "d". Counterbore 14, having a diameter larger than "d" is also reamed into the end 10a of holder rod 10. A tension eye 16 is drilled through holder rod 10 at opposite end 10b, transverse to axis X—X. Referring now to FIG. 2, insert rod 18 is shown in cross section. Insert rod 18 is also cylindrical in shape, having a diameter essentially equal to diameter "d" of bore 12. A second tension eye 20 is drilled through insert rod 18 at one end, transverse to longitudinal axis Y—Y of insert rod 18.

Referring now additionally to FIG. 3, there is shown a cross sectional view of rods 10 and 18 assembled for testing. The end of insert rod furthest from second tension eye 20 is inserted into bore 12 of holder rod 10 and seated against base 12a of bore 12 (shown in FIG. 1), such that the axes X—X and Y—Y of rods 10 and 18, respectively, are aligned. In preparing the rods for testing, adhesive 22 is first placed into bore 12 and counterbore 14 of holder rod 10. When insert rod 18 is placed within bore 10, adhesive 22 fills the space between insert rod 18 and counterbore 14, creating a uniformly thick, cylindrical adhesive bond between holder rod 10 and insert rod 18. Using tension eyes 16 and 20, a tensile load is applied along axes X—X and Y—Y, trying to pull insert rod 18 from within bore 12, which puts adhesive 22 into pure shear. In the preferred embodiment shown, an adhesive reservoir 24 is formed at base 12a by drilling further along axis X—X. A drain tap 26 is drilled into holder rod 10 transverse to axis X—X to intersect reservoir 24. When insert rod 18 is placed into bore 12 and counterbore 14, excess adhesive is allowed to flow through reservoir 24 and out drain tap 26. This allows full engagement of the insertion rod into the bore. The adhesive can also be flushed from drain tap 26 and reservoir 24 to prevent an adhesive bond at the end of the insertion rod along the direction of base 12a of bore 12. Teflon tape 28 is also applied to the end of insertion rod 18 to further prevent the formation of a bond. This will ensure that shear strength measurements are not influenced by a bond which would be subjected to a tensile load.

What has thus been described is an adhesive shear strength test apparatus having a cylindrical adhesive bond between test specimens which is subjected to pure shear. The test specimens are two cylindrical rods. One rod has a bore and counterbore reamed into one end along its longitudinal axis. The other rod has a diameter equal to the diameter of the bore. The adhesive to be tested is placed within the bore and counterbore and the smaller diameter rod is inserted into the bore. The adhesive fills the space between the smaller rod and the counterbore, creating a uniform, cylindrical layer of adhesive between the exterior surface of the smaller rod and the inner surface of the counterbore. When the adhesive cures, the assembly is subjected to a tensile load along its longitudinal axis tending to pull the inserted rod from the bore such that the adhesive is subjected to a pure shear load. The rods can be machined to tight tolerances to provide consistent adhesive thicknesses from test to test. Additionally, a number of test specimens can be fabricated with differing counterbore diameters to test the effect of adhesive thickness on shear strength. By fabricating the test specimens of metal, the adhesive can be baked off by placing the assembly in an oven, allowing the specimens to be used again. Obviously many modifications and variations of the present invention may become apparent in light of the above teachings. For example, the method of applying the tensile load can be varied to suit the testing apparatus so long as the load is applied axially. In the preferred embodiment, pins are placed through tension eyes drilled through the rods. However, eyes could be screwed into the ends of the rods, or a flange could be attached to provide a grip for a pulling device, or the rods may simply be gripped at their ends and pulled apart. Also, the preferred embodiment contemplates using mild steel rods but the rods may be fabricated of any suitable material which could be drilled as indicated.

In light of the above, it is therefore understood that within the scope of the appended claims, the invention may be practiced otherwise than as specifically described.

What is claimed is:

1. An adhesive shear strength test apparatus comprising:
   a first cylindrical rod having a bore of a certain diameter and a certain depth reamed into a first end along a longitudinal axis of the rod and having a counterbore of a diameter larger than the diameter of the bore reamed to a depth less than the depth of the bore into said first end along the longitudinal axis;
   a second cylindrical rod having a diameter essentially equal to the diameter of the bore, an insertion end of the second rod being inserted into the bore of the first rod, the second rod being aligned with the longitudinal axis of the first rod; and
   adhesive placed within a cylindrical space of uniform thickness formed between the second rod and an inner surface of the counterbore, the adhesive forming a bond between the first rod and the second rod such that the adhesive is subjected to a pure shear load when the first and second rods are subjected to a tensile load applied along the longitudinal axis.

2. The test apparatus of claim 1 further comprising:
   a first tension eye drilled through the first rod transverse to the longitudinal axis thereof and at an end opposite the first end; and
   a second tension eye drilled through the second rod transverse to a longitudinal axis thereof and at an end opposite the insertion end, the first and second tension eyes for applying the tensile load.

3. An adhesive shear strength test apparatus comprising:
   a first cylindrical rod having a bore of a certain diameter and a certain depth reamed into a first end along a longitudinal axis of the rod and having a counterbore of a diameter larger than the diameter of the bore reamed to a depth less than the depth of the bore into said first end along the longitudinal axis;
   a second cylindrical rod having a diameter essentially equal to the diameter of the bore, an insertion end of the second rod being inserted into the bore of the first rod, the second rod being aligned with the longitudinal axis of the first rod;
   adhesive placed within a cylindrical space formed between the second rod and an inner surface of the counterbore, the adhesive forming a bond between the first rod and the second rod such that the adhesive is subjected to a pure shear load when the first and second rods are subjected to a tensile load applied along the longitudinal axis;
   a reservoir of a diameter smaller than the diameter of the bore drilled to a depth greater than the depth of the bore into the first end of the first rod along the longitudinal axis thereof; and
   a drain tap drilled into the first end of the first rod transversely to the longitudinal axis thereof and intersecting the reservoir, the reservoir and drain tap allowing full engagement of the second rod within the bore by facilitating removal of excess adhesive and bleeding of air from the apparatus when the second rod is inserted into the bore.

4. The test apparatus of claim 2 further comprising:
   a reservoir of a diameter smaller than the diameter of the bore drilled to a depth greater than the depth of the bore into the first end of the first rod along the longitudinal axis thereof; and
   a drain tap drilled into the first end of the first rod transversely to the longitudinal axis thereof and intersecting the reservoir, the reservoir and drain tap allowing full engagement of the second rod within the bore by facilitating removal of excess adhesive and bleeding of air from the apparatus when the second rod is inserted into the bore.

5. The apparatus of claim 3 wherein the first and second rods are fabricated of metal.

6. The apparatus of claim 3 wherein a non-bonding agent is applied to the insertion rod to prevent the insertion rod from bonding to the bore in a direction transverse to the longitudinal axis.

7. The apparatus of claim 4 wherein a non-bonding agent is applied to the insertion rod to prevent the insertion rod from bonding to the bore in a direction transverse to the longitudinal axis.

8. A method for testing an adhesive bond in pure shear comprising the steps of:
   providing a cylindrical holder rod;
   reaming a bore of a certain diameter a distance from an end of the holder rod along a longitudinal axis thereof;
   reaming a counterbore of a diameter larger than the diameter of the bore to a lesser distance than the bore along the longitudinal axis of the holder rod;
   providing a cylindrical insertion rod having a diameter essentially equal to the diameter of the bore;
   providing adhesive within the counterbore;
   inserting the insertion rod through the adhesive in the counterbore and into the bore, the insertion rod being aligned with the longitudinal axis of the holder rod, the adhesive filling a cylindrical space of uniform thickness between the insertion rod and an inner surface of the counterbore;

allowing the adhesive to cure forming a cylindrical bond between the insertion rod and the inner surface of the counterbore;

subjecting the holder rod and the insertion rod to increasing tensile force tending to pull the insertion rod from within the bore of the holder rod, the tensile force being resisted by shear within the cylindrical bond; and measuring the strength of the shear until failure of the bond.

9. A method for testing an adhesive bond in pure shear comprising the steps of:

providing a cylindrical holder rod;

reaming a bore of a certain diameter a distance from an end of the holder rod along a longitudinal axis thereof;

reaming a counterbore of a diameter larger than the diameter of the bore to a lesser distance than the bore along the longitudinal axis of the holder rod;

drilling a reservoir of a diameter smaller than the diameter of the bore to a greater distance than the bore along the longitudinal axis of the holder rod;

drilling a drain tap transverse to the longitudinal axis of the holder rod intersecting with the reservoir;

providing a cylindrical insertion rod having a diameter essentially equal to the diameter of the bore;

providing adhesive within the counterbore;

inserting the insertion rod through the adhesive in the counterbore and into the bore, the insertion rod being aligned with the longitudinal axis of the holder rod, the adhesive filling a cylindrical space between the insertion rod and an inner surface of the counterbore;

allowing excess adhesive and air to flow through the reservoir and out of the drain tap as the insertion rod is inserted into the bore;

flushing excess adhesive from the reservoir and the drain tap when the insertion rod is fully within the bore;

allowing the adhesive to cure forming a cylindrical bond between the insertion rod and the inner surface of the counterbore;

subjecting the holder rod and the insertion rod to increasing tensile force tending to pull the insertion force being resisted by shear within the cylindrical bond; and measuring the strength of the shear until failure of the bond.

10. The method of claim 9 further comprising the steps of:

providing a plurality of comparison rods, each having a comparison bore of essentially the same diameter and depth as the bore of the holder rod and each having a comparison counterbore of essentially the same depth as the holder rod counterbore, the comparison counterbores having diameters differing from the holder rod counterbore and differing from each other;

sequentially substituting the comparison rods for the holder rod, the differing diameters resulting in differing adhesive bond thickness when the adhesive is provided within the comparison counterbores and the insertion rod is inserted into the comparison bores; and separately measuring the shear strength of the differing adhesive bond thicknesses for obtaining a range of adhesive bond shear strength for the differing adhesive bond thicknesses.

11. The method of claim 9 further comprising the step of applying a non-bonding agent to the insertion rod to prevent bonding of the insertion rod to the bore in a direction transverse to the longitudinal axis.

* * * * *